(12) United States Patent
Kohlrausch et al.

(10) Patent No.: US 9,693,739 B2
(45) Date of Patent: Jul. 4, 2017

(54) SYSTEMS AND METHODS FOR REDUCING THE IMPACT OF ALARM SOUNDS ON PATIENTS

(71) Applicant: KONINKLIJKE PHILIPS N.V., Eindhoven (NL)

(72) Inventors: Armin Gerhard Kohlrausch, Eindhoven (NL); Thomas Falck, Aachen (DE); Mun Hum Park, Eindhoven (NL); Sam Martin Jelfs, Riethoven (NL); Katja Leuschner, Rijswijk (NL)

(73) Assignee: Koninklijke Philips N.V., Eindhoven (NL)

( * ) Notice: Subject to any disclaimer, the term of this patent is extended or adjusted under 35 U.S.C. 154(b) by 0 days.

(21) Appl. No.: 14/771,517

(22) PCT Filed: Mar. 6, 2014

(86) PCT No.: PCT/IB2014/059477
§ 371 (c)(1),
(2) Date: Aug. 31, 2015

(87) PCT Pub. No.: WO2014/136069
PCT Pub. Date: Sep. 12, 2014

(65) Prior Publication Data
US 2016/0015329 A1    Jan. 21, 2016

(30) Foreign Application Priority Data

Mar. 6, 2013   (EP) .................................... 13158006

(51) Int. Cl.
*G08B 23/00*   (2006.01)
*A61B 5/00*    (2006.01)
(Continued)

(52) U.S. Cl.
CPC .............. *A61B 5/746* (2013.01); *A61B 5/002* (2013.01); *A61B 5/1113* (2013.01); *A61B 5/742* (2013.01);
(Continued)

(58) Field of Classification Search
CPC ....... A61B 5/746; A61B 5/742; A61B 5/6889; G06F 19/3406; G08B 21/22
(Continued)

(56) References Cited

U.S. PATENT DOCUMENTS 7,130,759 B2   10/2006  Willins et al.
7,920,061 B2 *  4/2011  Klein .................... A61B 5/1113
                                                 340/506
(Continued)

FOREIGN PATENT DOCUMENTS

CN         1187338 A     7/1998
CN       101496016 A     7/2009
(Continued)

*Primary Examiner* — Phung Nguyen

(57) ABSTRACT

There is provided a system for use with a patient in a healthcare environment, the system comprising a medical device configured to monitor or treat a patient, the medical device being for use in a room in which the patient is located and comprising an alarm unit configured to issue an audible alarm; a detection unit configured to detect whether a healthcare staff member is in the room in which the patient is located; a remote alarm unit configured to issue an alarm to alert a healthcare staff member located outside the room in which the patient is located; and a control unit that is connected to the medical device, the remote detection unit and the alarm unit, the control unit being configured to: (i) control the alarm unit in the medical device to issue an audible alarm in the event that the medical device detects an alarm condition for the patient or the medical device and the detection unit detects that a healthcare staff member is in the room in which the patient is located; and (ii) control the (Continued)

remote alarm unit to issue an alarm to alert a healthcare staff member located outside the room in which the patient is located in the event that the medical device detects an alarm condition for the patient or the medical device and the detection unit detects that no healthcare staff member is in the room in which the patient is located.

13 Claims, 8 Drawing Sheets

(51) Int. Cl.
    *A61B 5/11*     (2006.01)
    *G08B 3/10*     (2006.01)
    *G08B 21/22*     (2006.01)
    *A61G 7/002*     (2006.01)
    *G06F 19/00*     (2011.01)

(52) U.S. Cl.
    CPC ......... *A61G 7/002* (2013.01); *G06F 19/3418* (2013.01); *G08B 3/10* (2013.01); *G08B 21/22* (2013.01); *A61B 5/7405* (2013.01)

(58) Field of Classification Search
    USPC ... 340/541, 573.1, 573.4, 572.1, 10.1, 13.24
    See application file for complete search history.

(56) References Cited

U.S. PATENT DOCUMENTS

| | | |
|---|---|---|
| 8,184,824 B2 | 5/2012 | Hettinger et al. |
| 2005/0035862 A1* | 2/2005 | Wildman ............... A61B 5/1113 340/573.1 |
| 2005/0099824 A1 | 5/2005 | Dowling et al. |
| 2005/0146431 A1 | 7/2005 | Hastings et al. |
| 2006/0098830 A1 | 5/2006 | Roeder et al. |
| 2007/0080801 A1* | 4/2007 | Weismiller ............. A61B 5/411 340/539.13 |
| 2007/0177744 A1* | 8/2007 | Kirn ......................... H03G 3/30 381/107 |
| 2011/0085680 A1 | 4/2011 | Chen et al. |
| 2012/0013465 A1* | 1/2012 | Reeder ................. A61B 5/0002 340/541 |
| 2012/0027226 A1 | 2/2012 | Desenberg |
| 2012/0148053 A1 | 6/2012 | Tan et al. |

FOREIGN PATENT DOCUMENTS

| | | |
|---|---|---|
| JP | 2009218888 A | 9/2009 |
| WO | 2014140053 A1 | 9/2014 |

* cited by examiner

SYSTEMS AND METHODS FOR REDUCING THE IMPACT OF ALARM SOUNDS ON PATIENTS

TECHNICAL FIELD OF THE INVENTION

The invention relates to medical devices at the point of care used to, for example, monitor and/or treat patients in a hospital or nursing home environment, and in particular to systems and methods for reducing the impact that audible alarms issued by these medical devices have on patients.

BACKGROUND TO THE INVENTION

Many medical devices used in intensive care units of hospitals provide acoustic (audible) alarms, if specific conditions or events occur. The medical device or devices are typically arranged near to a patient's bed and are for monitoring one or more physiological characteristics of a patient, such as heart rate, blood pressure, breathing rate, blood oxygen levels, etc, and/or for providing some treatment to a patient, such as controlling the administration of an intravenous drug, assisting the patient's breathing, etc. The specific conditions that lead to alarms being triggered can refer to, for example, abnormal values of the physiological characteristics of the patient or specific operating states or error states of the device.

The alarms issued by these devices are primarily for the attention of the healthcare staff in the hospital and serve to acoustically alert staff members to direct their attention to the device and take any appropriate or required action. Although the alarm sound level for a particular medical device may be able to be set by the end users (the healthcare staff) to specific levels, these levels will typically stay fixed after being set during installation, which means that alarm sounds are played with a fixed absolute sound power level. This level will have been set sufficiently high to guarantee that healthcare staff will be alerted despite the environment in which the medical device is being used being very noisy (for example if many staff members are speaking simultaneously and/or if there are lots of noisy medical devices being used). In some cases, the level can be set sufficiently high so that the alarm can be clearly heard outside the room in which the patient is located, which means that the alarm will be particularly loud for a patient that is lying next to the medical device.

It has been found that alarm sounds issuing from medical devices associated with a particular patient have a strong negative impact on the recovery of that patient and any nearby patients since the alarms lead to increased anxiety in the patient and sleep interruptions. This problem is particularly evident for patients in an intensive care unit where there may be many different medical devices associated with each patient, each having their own alarm sounds and volumes.

Therefore, there is a need for systems and methods for reducing the negative impact that these alarm sounds have on patients while ensuring that healthcare staff are still adequately alerted.

SUMMARY OF THE INVENTION

According to a first aspect of the invention, there is provided a system for use with a patient in a healthcare environment, the system comprising a medical device configured to monitor or treat a patient, the medical device being for use in a room in which the patient is located and comprising an alarm unit configured to issue an audible alarm; a detection unit configured to detect whether a healthcare staff member is in the room in which the patient is located; a remote alarm unit configured to issue an alarm to alert a healthcare staff member located outside the room in which the patient is located; and a control unit that is connected to the medical device, the remote detection unit and the alarm unit, the control unit being configured to: (i) control the alarm unit in the medical device to issue an audible alarm in the event that the medical device detects an alarm condition for the patient or the medical device and the detection unit detects that a healthcare staff member is in the room in which the patient is located; and (ii) control the remote alarm unit to issue an alarm to alert a healthcare staff member located outside the room in which the patient is located in the event that the medical device detects an alarm condition for the patient or the medical device and the detection unit detects that no healthcare staff member is in the room in which the patient is located.

In some embodiments, the control unit is further configured to prevent the alarm unit in the medical device from issuing an audible alarm in the event that the control unit controls the remote alarm unit to issue the alarm to alert a healthcare staff member. This embodiment provides the advantage that the patient is not disturbed at all by an alarm triggered by the medical device.

In alternative embodiments, the control unit is configured to control the alarm unit in the medical device to issue an audible alarm at a first volume level in the event that the medical device detects an alarm condition for the patient or the medical device and the detection unit detects that a healthcare staff member is in the room in which the patient is located; and wherein the control unit is further configured to control the alarm unit in the medical device to issue an audible alarm at a second volume level in the event that the control unit controls the remote alarm unit to issue the alarm to alert a healthcare staff member, wherein the second volume level is lower than the first volume level. This embodiment provides the advantage that the disturbance to the patient can be kept to a minimum (while still generating an alarm near to the patient), until a healthcare staff member is present to attend to and reassure the patient.

In some embodiments, the control unit is configured such that, if following the issue of an alarm by the remote alarm unit the detection unit detects that a healthcare staff member is in or has entered the patient room, the control unit controls the remote alarm unit to cease the issue of the alarm and controls the alarm unit in the medical device to issue an audible alarm.

In preferred embodiments, the remote alarm unit comprises an alarm unit configured to issue an audible alarm. Preferably, in these embodiments, the remote alarm unit is located outside of the room in which the patient/medical device is located. In some cases the remote alarm unit can be located immediately outside the room, and in other cases the remote alarm unit can be located in another room, for example a staff room.

In some embodiments, the remote alarm unit further comprises a visual indicator that is configured to be activated when the alarm unit in the remote alarm unit is controlled to issue an audible alarm. In some embodiments, the control unit is configured to modulate the luminance of the visual indicator coherently with the volume of the audible alarm.

In preferred embodiments the control unit is further configured to adjust or set the volume of the audible alarm issued by the remote alarm unit based on the distance of a healthcare staff member from the room in which the patient is located.

In those embodiments the detection unit may be further configured to detect the distance of the healthcare staff member from the room in which the patient is located.

In further or alternative embodiments the system may further comprise a second detection unit configured to detect the distance of the healthcare staff member from the room in which the patient is located.

In some embodiments the control unit can be configured to reduce the volume of the audible alarm issued by the remote alarm unit as the distance of the healthcare staff member from the room in which the patient is located decreases.

In some embodiments the control unit can be configured to increase the volume of the audible alarm issued by the remote alarm unit as the distance of the healthcare staff member from the room in which the patient is located increases.

In some embodiments the control unit is configured to set the volume of the audible alarm issued by the remote alarm unit to a first level when the healthcare staff member is a first distance from the room in which the patient is located and a second level when the healthcare staff member is a second distance from the room in which the patient is located, wherein the first level is greater than the second level and the first distance is greater than the second distance.

In other embodiments the control unit is configured to set the volume of the audible alarm issued by the remote alarm unit to a first level when the healthcare staff member is greater than a threshold distance from the room in which the patient is located, and a second (lower) level when the healthcare staff member is less than the threshold distance from the room in which the patient is located.

In some embodiments, the system further comprises a second detection unit configured to detect the location of a healthcare staff member relative to the room in which the patient is located; and the control unit is configured to adjust the volume of the audio alarm issued by the remote alarm unit based on the output of the second detection unit.

In some alternative or additional embodiments, the remote alarm unit can be configured to issue an alarm to alert a healthcare staff member located outside the room in which the patient is located by transmitting a message, paging message or actuation signal to a device carried or worn by a healthcare staff member.

In preferred embodiments, the detection unit comprises one or more of a radio frequency identification, RFID, tag reader, a near-field communication, NFC, tag reader and a camera.

In alternative embodiments, the detection unit is configured to detect the location of the healthcare staff member, and in particular the presence of a healthcare staff member in the room in which the patient is located, by triangulating the location of healthcare staff members using wireless communication-enabled devices carried by the healthcare staff members.

According to a second aspect of the invention, there is provided a method of operating a system for use with a patient in a healthcare environment, the method comprising determining whether a healthcare staff member is in the room in which a medical device that is monitoring or treating a patient is located; and in the event that an alarm condition for the patient or medical device is detected: (i) issuing an audible alarm from an alarm unit in the medical device if it is determined that a healthcare staff member is in the room in which the patient is located; and (ii) issuing an alarm to alert a healthcare staff member located outside the room in which the patient is located if it is determined that no healthcare staff member is in the room in which the patient is located.

In some embodiments, in the event that an alarm condition for the patient or medical device is detected and it is determined that no healthcare staff member is in the room in which the patient is located, the method further comprises preventing an alarm unit in the medical device from issuing an audible alarm.

In alternative embodiments, step (i) comprises issuing the audible alarm from the alarm unit at a first volume level, and wherein step (ii) further comprises issuing an audible alarm from the alarm unit in the medical device at a second volume level, wherein the second volume level is lower than the first volume level.

In some embodiments, following the issue of an alarm according to step (ii), if it is determined that a healthcare staff member is in or has entered the patient room, the method further comprises the step of stopping the issue of the alarm used to alert a healthcare staff member located outside the room in which the patient is located and issuing an audible alarm from the alarm unit in the medical device.

Preferably step (ii) comprises issuing an audible alarm.

In some embodiments, step (ii) further comprises activating a visual indicator. In some embodiments, step (ii) further comprises modulating the luminance of the visual indicator coherently with the volume of the audible alarm.

In preferred embodiments the method further comprises determining the location of a healthcare staff member relative to the room in which the patient is located (and in particular the distance of the healthcare staff member from the room); and adjusting or setting the volume of the audible alarm issued by the remote alarm unit based on the determined distance.

In some embodiments the step of adjusting or setting comprises reducing the volume of the audible alarm issued by the remote alarm unit as the distance of the healthcare staff member from the room in which the patient is located decreases.

In some embodiments the step of adjusting or setting further or alternatively comprises increasing the volume of the audible alarm issued by the remote alarm unit as the distance of the healthcare staff member from the room in which the patient is located increases.

In some embodiments the step of adjusting or setting comprises setting the volume of the audible alarm issued by the remote alarm unit to a first level when the healthcare staff member is a first distance from the room in which the patient is located and a second level when the healthcare staff member is a second distance from the room in which the patient is located, wherein the first level is greater than the second level and the first distance is greater than the second distance.

In other embodiments the step of adjusting or setting comprises setting the volume of the audible alarm issued by the remote alarm unit to a first level when the healthcare staff member is greater than a threshold distance from the room in which the patient is located, and a second (lower) level when the healthcare staff member is less than the threshold distance from the room in which the patient is located.

According to a third aspect of the invention, there is provided a computer program product, comprising computer readable code embodied therein, the computer readable code being configured such that, on execution by one or more suitable computers or processing units, the one or more suitable computers or processing units are caused to execute the steps in any of the methods described above.

According to a fourth aspect of the invention, there is provided a medical device for use in monitoring or treating a patient in a patient bed, the position and/or configuration of the patient bed being adjustable to the needs of the patient, the medical device being for use in a room in which the patient bed is located, the medical device comprising a sensor configured to monitor the patient and/or the operation of the medical device; a directional speaker configured to emit an alarm signal in the event that the sensor detects an alarm condition for the patient or the medical device, the directional speaker being configured to emit the alarm signal with spatial directivity such that the alarm signal is emitted substantially away from (or not generally in the direction of) a patient on the patient bed; a control unit that is configured to determine the position and/or configuration of the patient bed or changes in the position and/or configuration of the patient bed and to adjust the spatial directivity of the directional speaker in response to changes in the position and/or configuration of the patient bed so that the alarm signal is emitted substantially away from (or not generally in the direction of) a patient on the patient bed.

In some embodiments, the control unit is configured to adjust the spatial directivity of the directional speaker in one or both of the horizontal and vertical directions.

In some embodiments, the directional speaker comprises an array of speakers. The directivity of the array of speakers can be adjusted by changing gain factors, frequency response and/or delays in signals sent from the control unit for individual ones of the speakers in the array. In addition or alternatively, the directivity of the directional speaker can be adjusted by physically moving the speaker.

In some embodiments, the changes in the position and/or configuration of the patient bed include the raising and lowering of the height of the bed and/or adjusting the bed such that the patient is lying down or sitting up.

According to a fifth aspect of the invention, there is provided a method of operating a medical device for use in monitoring or treating a patient in a patient bed, in which the position and/or configuration of the patient bed is adjustable to the needs of the patient, the medical device being for use in a room in which the patient bed is located, the medical device comprising a directional speaker configured to emit an alarm signal with spatial directivity; the method comprising determining the position and/or configuration of the patient bed or changes in the position and/or configuration of the patient bed, and in the event that an alarm condition for the patient or medical device is detected, adjusting or setting the spatial directivity of the directional speaker in response to the position and/or configuration of the patient bed or changes in the position and/or configuration of the patient bed so that the alarm signal is emitted substantially away from (or not generally in the direction of) a patient on the patient bed.

BRIEF DESCRIPTION OF THE DRAWINGS

For a better understanding of the invention, and to show more clearly how it may be carried into effect, reference will now be made, by way of example only, to the accompanying drawings, in which.

DETAILED DESCRIPTION OF THE PREFERRED EMBODIMENTS

Figure 1:
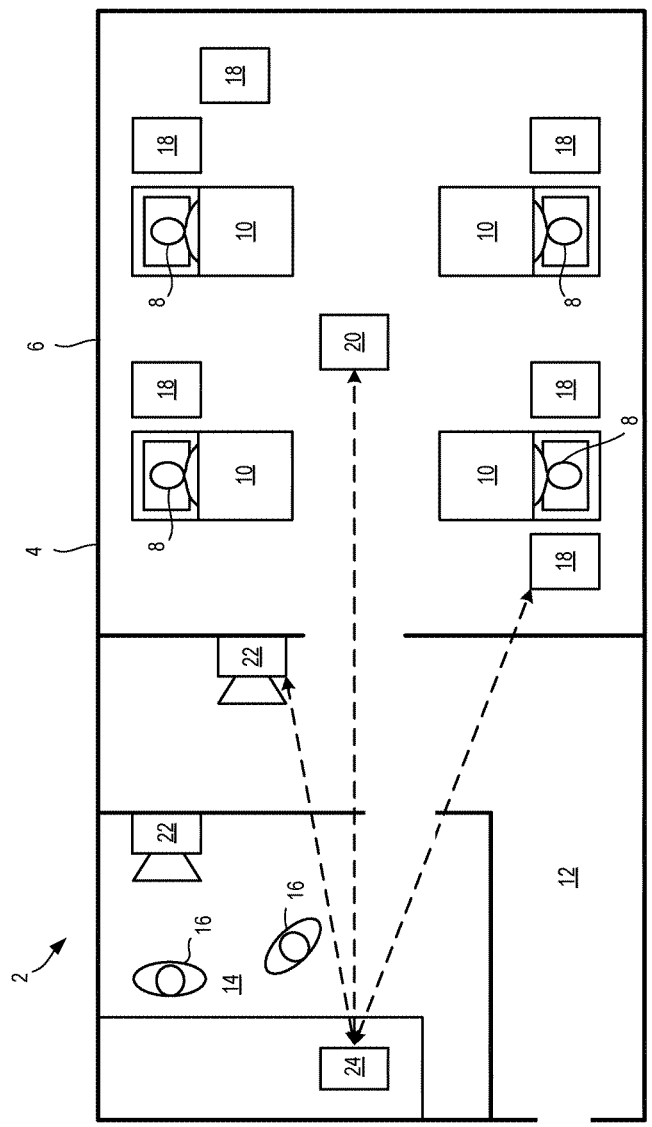
FIG. 1 is an illustration of a system according to a first aspect of the invention in a healthcare environment.
Figure 2:
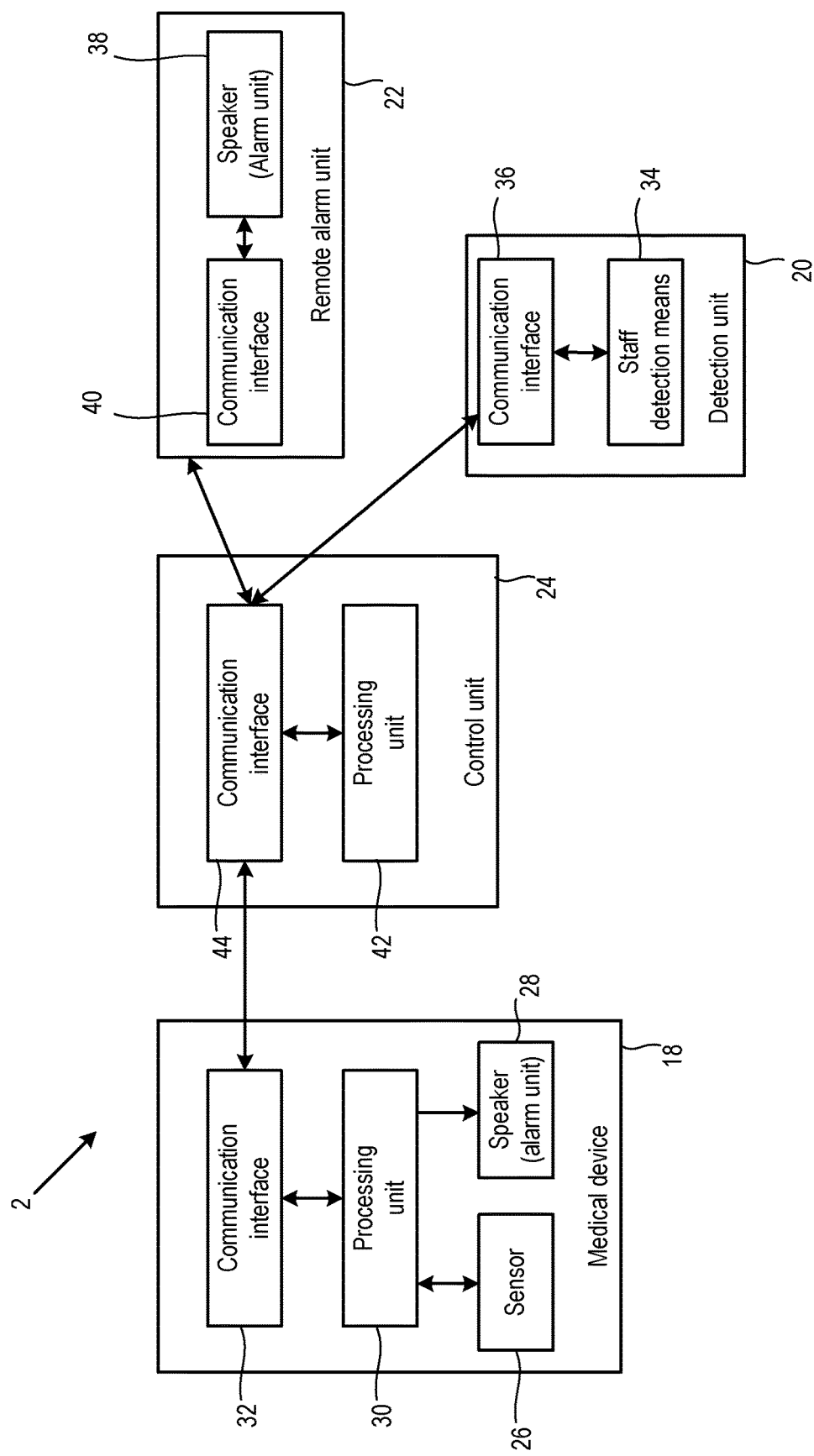
FIG. 2 is a block diagram of the system shown in FIG. 1.

FIG. 1 is an illustration of a system 2 according to a first aspect of the invention in a healthcare environment 4 (such as a hospital or nursing home). FIG. 2 is a block diagram of that system 2. Briefly, in accordance with this aspect of the invention, the system 2 comprises a unit that is configured to detect whether a healthcare staff member is present in the same room as the medical device (and patient). When the medical device is to trigger an alarm, an audible alarm is generated by a speaker in the medical device if the detection unit determines that a healthcare staff member is in the same room as the medical device. However, if the detection unit determines that no healthcare staff member is present in the room, the alarm is issued by a remote alarm unit that is located somewhere outside the room in which the medical device and patient are located (for example the remote alarm unit can be located immediately outside the room in a corridor or another room, or at a nearby staff workstation). When the alarm is issued by the remote alarm unit, the medical device can be controlled such that it does not generate the audible alarm itself or generates the alarm at a reduced volume, thereby avoiding or reducing the disturbance to the patient and reducing the overall impact of the alarms on the patient.

In the example of FIG. 1, the hospital or nursing home environment 4 comprises a patient room 6 in which patients 8 are located in respective beds 10, a corridor 12 outside the patient room 6 and a workstation or room 14 for the healthcare staff 16.

Each patient 8 has one or more medical devices 18 associated with them. Each medical device 18 is used at the point of care and can be for monitoring one or more physiological characteristics of the patient 8, such as heart rate, blood pressure, breathing rate, blood oxygen levels, etc, and/or for providing some treatment to the patient 8, such as controlling the administration of an intravenous drug, assisting the patient's breathing, etc. Another type of medical device 18 in which the invention can be used is a patient monitor.

In addition to the medical devices 18, the system 2 comprises one or more detection units 20 for detecting whether there are any healthcare staff members 16 in the patient room 6, one or more remote alarm units 22 located somewhere outside the patient room 6 in which the patients 8 and medical devices 18 are located and a control unit 24. The medical devices 18, detection unit 20 and remote alarm units 22 are each connected to the control unit 24 using wires or a short or long-range wireless technology, such as Wi-Fi, Bluetooth, ZigBee, or a cellular telecommunications network, etc.

In this illustrated embodiment, a first remote alarm unit 22 that is configured to generate an audible alarm is located immediately outside the patient room 6, a second remote alarm unit 22 that is configured to generate an audible alarm is located at the staff workstation 14, the detection unit 20 is located in the patient room 6 (with the exact location in the patient room 6 depending on the modality the detection unit 20 uses to detect the presence of healthcare staff members 16 in the room 6), and the control unit 24 is located at the staff workstation 14, although it will be appreciated that different positioning and arrangements of the units in the system 2 are contemplated (for example the control unit 24 can be implemented as part of a central monitoring station in the hospital). For example, it is possible to combine the functionality of one or more of the medical devices 18, detection unit 20, remote alarm unit 22 and control unit 24 into a single device.

Referring to FIG. 2, some of the components of each of the units in the system 2 are shown. It will be appreciated that only the components of the units that are useful for illustrating the invention are shown in FIG. 2, and that in practice the units will comprise additional components.

The medical device 18 comprises at least one sensor 26 for monitoring one or more physiological characteristics of the patient 8 and/or for monitoring the operation of the medical device 18 (as appropriate depending on the purpose of the medical device). The medical device also comprises a processing unit 30 that is connected to the at least one sensor 26 and that controls the operation of the medical device 18. A speaker or audible alarm unit 28 is provided that is connected to the processing unit 30 and that is used to generate an audible alarm signal in response to an alarm condition being detected by the sensor 26 and processing unit 30 (although in alternative embodiments the output of the sensor 26 can be provided to the control unit 24 and the control unit 24 can determine whether an alarm condition exists). A communication interface 32 is provided that is connected to the processing unit 30 and that enables communications between the medical device 18 and the control unit 24.

The detection unit(s) 20 comprise staff detection means which detect whether there are any healthcare staff members 16 in the patient room 6 using any suitable technology. For example, the detection means 34 can comprise an antenna and control circuitry for detecting radio-frequency identification (RFID) tags or near-field communication (NFC) tags that are carried or worn by healthcare staff members 16. In this case, the detection unit 20 (or at least the antenna) may be positioned in the patient room 6 so that it only detects tags when they are present in the room 6 or enter the room 6. Alternatively, the staff detection means 34 can use other types of indoor tracking technology, for example based on triangulation using Wi-Fi or Zigbee-enabled devices carried by the staff members 16, or using cameras and image processing technology to determine if a staff member 16 is present in the room 6. The detection unit 20 also comprises a communication interface 36 that is connected to the staff detection means 34 and that enables communications between the detection unit 20 and the control unit 24.

The remote alarm unit 22 comprises an alarm unit 38, which, in a preferred embodiment, is in the form of a speaker for generating an audible alarm signal for alerting staff members 16, and a communication interface 40 that enables communications between the remote alarm unit 22 and the control unit 24. In some embodiments, the alarm unit 38 may further include a light source that is illuminated or flashed to indicate the alarm condition. In other or further embodiments, the alarm unit 38 may alternatively or additionally alert the staff members 16 to the alarm condition by sending a message or alarm signal to a pager or mobile communication device (e.g. a mobile telephone) carried by the staff members 16, by sending an actuation signal to a bracelet or other device worn or carried by the staff members 16 that use haptic stimulation to alert the wearer to the alarm condition, etc. In these alternative embodiments, the alarm unit 38 will be in a suitable form (such as a transmitter) for transmitting the required message or control signals to the devices carried by the staff members 16.

In the embodiments where a signal is transmitted to devices carried by staff members 16 and the remote alarm unit 22 is not required to generate an audible alarm to alert the staff members 16, the alarm unit 38 in the remote alarm device 22 will comprise a transmitter for sending the required signals to the staff member devices, and it will be appreciated that it is not strictly necessary for the remote alarm unit 22 to be physically located outside of the patient room 6 (although this is of course possible).

In some embodiments, the speaker 38 in the remote alarm unit 22 is preferably configured to replicate the alarm sound generated by the medical device 18 to enable a staff member 16 located outside the patient room 6 to recognize the alarm sound and determine the reason for the alarm being issued.

The control unit 24 comprises a processing unit 42 that processes signals received from the medical device(s) 18 and detection unit(s) 20 and controls the alarm unit 28 in the medical device 18 and the alarm unit 38 in the remote alarm unit 22 to generate an alarm signal as appropriate in the event that an alarm condition is detected in or by the sensor 26 in the medical device 18. The control unit 24 also comprises a communication interface 44 that enables communications between the control unit 24 and each of the medical device(s) 18, detection unit(s) 20 and remote alarm unit(s) 22.

Figure 3:
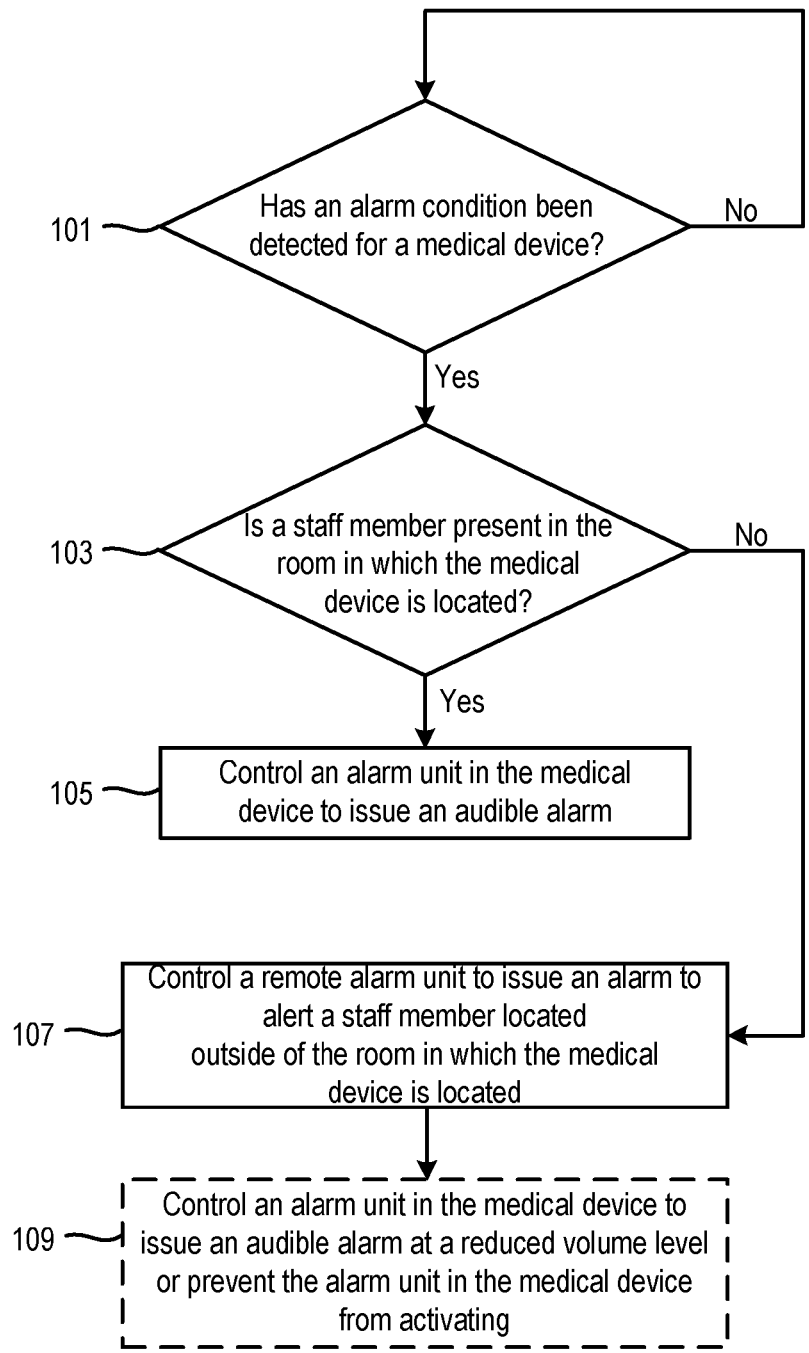
FIG. 3 is a flow chart illustrating a method of operating a control unit in the system shown in FIG. 1.

FIG. 3 illustrates a method of operating the control unit 24 of the system 2 shown in FIG. 1 in accordance with this aspect of the invention. In a first step, step 101, the control unit 24 (or rather the processing unit 42 in the control unit 24) determines whether an alarm condition has been detected for a medical device 18. In some embodiments, the processing unit 30 in the medical device 18 can determine whether an alarm condition exists on the basis of the output of the sensor 26 and communicate the existence of the alarm condition to the processing unit 42 in the control unit 24. In alternative embodiments, the output of the sensor 26 can be passed to the processing unit 42 in the control unit 24 which itself evaluates the output signal to determine if an alarm condition exists.

Step 101 repeats until an alarm condition exists.

If an alarm condition has been detected, the method moves to step 103 in which it is determined whether a staff member 16 is present in the patient room 6 in which the medical device 18 that is experiencing the alarm condition is located. The control unit 24 determines this on the basis of the signals received from the detection unit 20. For example, where the detection unit 20 being used by the system 2 is based on RFID or NFC tag technology, the control unit 24 can determine that a staff member 16 is present in the patient room 6 if an RFID tag or NFC tag carried by staff members 16 is detected by an antenna in the patient room or detected by an antenna placed near to the door of the patient room 6 that detects the tag as the staff member 16 enters or leaves the room 6.

If the control unit 24 determines that a staff member 16 is present in the room 6 in which the medical device 18 is located, the control unit 24 sends a signal to the medical device 18 to cause the alarm unit 28 in the medical device 18 to generate an audible alarm signal (step 105). In response to receiving this signal, the processing unit 30 in the medical device 18 controls the speaker (or other alarm generating unit) 28 to generate the audible alarm to alert the staff member 16 present in the patient room 6. The audible alarm generated by the medical device 18 can be generated at a default or standard volume for the alarm.

As a staff member 16 is present in the patient room 6, the remote alarm unit 22 is not required to generate an alarm itself (although it will be appreciated that in some embodiments the remote alarm unit 22 could also be controlled to issue an alarm).

However, if in step 103 the control unit 24 determines that a staff member 16 is not present in the room 6 in which the medical device 18 is located when the alarm condition is detected, the control unit 24 sends a signal to a remote alarm unit 22 that causes the remote alarm unit 22 to alert staff members 16 that are outside of the patient room 6 (step 107).

In the preferred embodiments in which the remote alarm unit 22 comprises a speaker 38 for generating an audible alarm and the remote alarm unit 22 is located outside of the patient room 6 (for example located immediately outside the patient room 6 in the corridor 12 or located at the staff workstation 14), step 107 comprises sending a signal to the remote alarm unit 22 to cause the speaker 38 in the remote alarm unit 22 to generate an audible alarm signal. If there are multiple remote alarm units 22 in the system 2, step 107 can comprise sending a signal to one or more of those remote alarm units 22 to cause those remote alarm units 22 to generate an alarm. In some embodiments where the specific or general location of the staff members 16 outside the patient room 6 is known, then only a remote alarm unit 22 close to those staff members 16 can be controlled to generate an audible alarm.

In embodiments where the remote alarm unit 22 alerts staff members 16 to the alarm condition by sending a message or alarm signal to a pager, mobile communication device (e.g. a mobile telephone) or a device that uses haptic stimulation (and where conceivably the remote alarm unit 22 could be integrated with the control unit 24 which may be located in the patient room 6), it will be appreciated that the signal sent by the control unit 24 to the transmitter 38 in the remote alarm unit 22 causes the transmitter 38 to transmit or broadcast an appropriate message or signal outside the patient room 6 to cause the devices carried by the staff members 16 to alert those staff members 16 to the alarm condition.

In some embodiments, in the event that the remote alarm unit 22 is used to issue an alarm to alert staff members 16 to the alarm condition in step 107, the control unit 24 can send a signal to the medical device 18 that causes the processing unit 30 in the medical device 18 to mute the audible alarm signal generated by the speaker 28 (or prevent the speaker 28 from generating an audible alarm signal in the first place), which means that the patient 8 will not be disturbed when the alarm condition arises (step 109). Alternatively, the control unit 24 can send a signal to the medical device 18 that causes the speaker 28 to generate an audible alarm signal at a lower volume than the volume that would be used if a staff member 16 was already present in the patient room 6 (i.e. an alarm issued according to step 105), so that the staff member 16, when they enter the patient room 6, can identify the medical device 18 that is experiencing the alarm condition. Even in this implementation, the impact of the audible alarm on the patient 8 is much less than in conventional systems.

A further advantage of the system 2 according to this aspect of the invention is that, even when the medical device 18 generates the audible alarm according to step 105, as it is not necessary for that alarm to alert staff members 16 that are outside of the patient room 6 (since the alarm is used according to this step when a staff member 16 is present in the patient room 6), the default or standard volume of the audible alarm can be set at a lower level than in conventional systems where the alarm has to be set loud enough to alert staff members 16 that are potentially located outside of the patient room 6 (which further reduces the negative impact these alarms have on patients 8).

In some embodiments, following step 107 (or step 109), once a staff member 16 enters the room 6 (as detected by the detection unit 20), the control unit 24 can send a signal to the remote alarm unit 22 that causes the remote alarm unit 22 to stop generating an alarm, and can send a signal to the medical device 18 that causes the speaker 28 in the medical device 18 to start generating an audible alarm (if the speaker 28 was not already generating an alarm) or to generate the audible alarm at an increased volume (if the speaker 28 in the medical device 18 was already generating an audible alarm but at a reduced volume level).

In some implementations of this aspect of the invention, for example where there are many different patient rooms 6, each with a remote alarm unit 22 located outside of the door to the room 6, it may be difficult for a staff member 16 to easily identify the room to which the alarm relates (since it is perceptually difficult for a staff member 16 to directly identify from a distance which of a number of remote alarm units 22 is active). In this case, the remote alarm units 22 can be provided with a light or other visual indicator that can be activated when the audible alarm is generated to help guide the staff member 16 to the appropriate room 6. In some embodiments, the luminance of the light can be modulated coherently with the sound level of the audible alarm, which leads to strong binding of visual and acoustic stimulus in the observer's cognitive system, and the staff member 16 can, on approaching the appropriate room 6, interpret the audible alarm signal as code for the meaning of or reason for the alarm condition, and use the modulated lamp to identify the correct room.

These embodiments are particularly of use in an environment where there are a plurality of patient rooms in which multiple types of medical device 18 can be used for monitoring several patients, and where those medical devices 18 are capable of issuing different (i.e. audibly different) types of alarms to each other. A healthcare staff member 16 will be trained to recognize the sound of these alarms and the reason that they are issued, and thus determine which alarm has the highest priority (i.e. the alarm that should be dealt with first) if multiple alarms are issuing at the same time. For example a particular alarm sound may be issued by a breathing monitor if it detects an absence of a breath for a certain period of time, while an infusion pump may issue a different alarm sound when a medication infusion cycle has been completed. In this example, if both alarms are being issued at the same time, the healthcare staff member will recognize the distinct alarms and appreciate that the alarm from the breathing monitor should be dealt with first. The luminance of the visual indicators on the respective remote alarm units 22 will be modulated coherently with the volume of the audible alarm issued by that remote alarm unit 22, which means that, if the alarms are being issued from different patient rooms, the staff member 16 will be able to identify the room from which the breathing monitor alarm is being issued by identifying the visual indicator on the remote alarm unit 22 that is being illuminated coherently with the sound level of the relevant alarm (e.g. the breathing monitor alarm in this embodiment). In this embodiment, the speaker 38 in the remote alarm unit 22 is preferably configured to replicate the alarm sound generated by the medical device 18 to enable the staff member 16 to recognize the alarm sound and determine the reason for the alarm being issued.

In further embodiments, when a staff member 16 is approaching the correct room 6 (for example as detected by the detection unit 20 located in the patient room or by one or more detection units 20 located outside the patient rooms 6), the audible alarm could be controlled so that volume of the alarm is reduced (for example in a stepwise manner), which provides intuitive feedback that the staff member 16 is moving in the right direction. Likewise, the volume could be increased if the staff member 16 moves away from the relevant room 6.

The detection unit 20 located in the patient room 6 and/or one or more detection units 20 located outside the patient room 6 can be used to detect the location of a staff member 16 (for example using triangulation or other tracking technologies as described above), and the control unit 24 can determine the distance of the staff member 16 from the relevant patient room 6 (i.e. the room for which the audible alarm is being issued) from the detected location and the known location of the patient room 6. The control unit 24 can then determine and set the volume of the audible alarm issued by the remote alarm unit 22 based on the determined distance. Preferably the control unit 24 is configured to control the remote alarm unit 22 to decrease the volume of the audible alarm from the remote alarm unit 22 as the staff member 16 moves closer to the patient room 6 (and also to increase the volume of the audible alarm from the remote alarm unit 22 as the staff member 16 moves away from the patient room 16). As noted above, the volume can be decreased or increased in a stepwise manner, and may be decreased or increased in a generally linear manner with respective decreases or increases in the distance of the staff member 16 from the patient room.

In one example, when the staff member 16 is a first distance from the patient room 16 the control unit 24 can control the remote alarm unit 22 to issue the audible alarm with a first (non-zero) volume level, and when the staff member 16 is a second (smaller) distance from the patient room 16 the control unit 24 can control the remote alarm unit 22 to issue the audible alarm with a second (lower, but non-zero) volume level.

In another example, when the staff member 16 is greater than a threshold distance from the patient room 16, the control unit 24 can control the remote alarm unit 22 to issue the audible alarm with a first (non-zero) volume level, and when the staff member 16 is less than the threshold distance from the patient room 16 the control unit 24 can control the remote alarm unit 22 to issue the audible alarm with a second (lower, but non-zero) volume level.

As is known in the art, the sound in an enclosed space attenuates around 6 dB every doubling of the distance from a sound source up to a certain range, referred to as the 'critical distance', and then remains the same beyond that distance due to reverberation. The sound attenuation inside a room or space is affected by many factors (e.g. geometry of the space, the acoustic characteristics of the building materials, etc.), so the critical distance can typically only be determined through actual measurements or simulations.

Thus, in the exemplary embodiments above, the first volume level could be set to 80 dB, and the second volume level could be set to a value that is less than 80 dB and equal to or greater than 50 dB. In the first exemplary embodiment above, the first distance can be greater than the critical distance (or an estimation of the critical distance), with the second distance being a distance that is less than the critical distance (or an estimation of the critical distance). In the second exemplary embodiment the threshold distance can be the critical distance (or an estimation of the critical distance) from the remote alarm unit 22 located outside the room.

In embodiments where the volume can be decreased or increased in a stepwise or generally linear manner with respective decreases or increases in the distance of the staff member 16 from the patient room, the volume can be set according to the values in the following table:

| Sound volume (sound pressure) [dB] | distance [m] |
|---|---|
| 50 | 0.5 |
| 56 | 1 |
| 62 | 2 |
| 68 | 4 |
| 74 | 8 |
| 80 | 16 (=critical distance) |
| 80 | >16 |

Therefore, there is provided a system and method for reducing the negative impact that alarm sounds have on patients while ensuring that healthcare staff are still adequately alerted.

Figure 4:
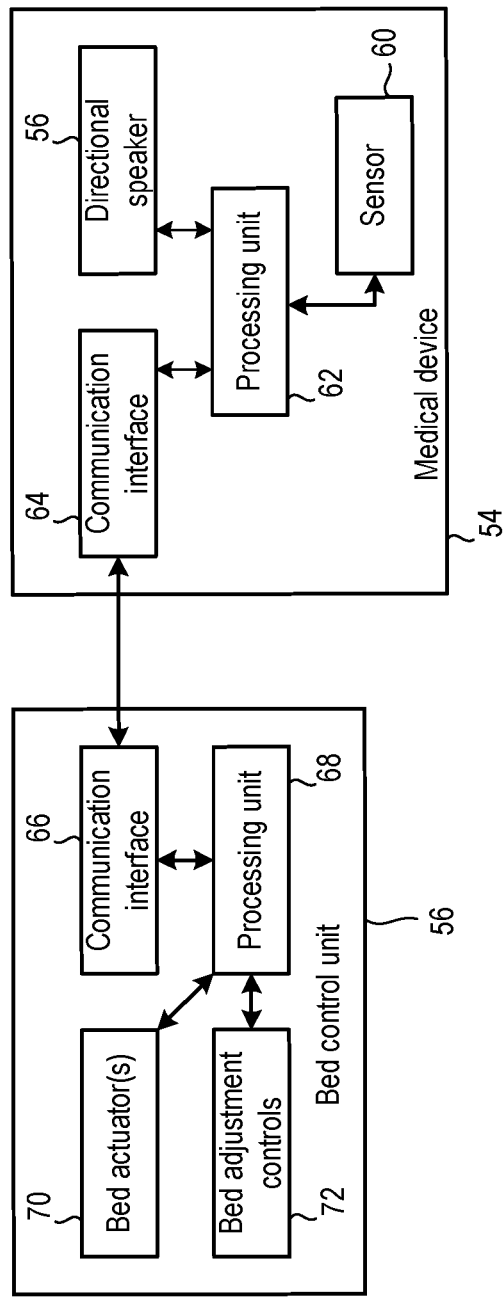
FIG. 4 is a block diagram of a system according to another aspect of the invention.

A block diagram of a system 52 according to another aspect of the invention is shown in FIG. 4. It will be appreciated that this aspect of the invention can be implemented in a medical device within a healthcare environment in conjunction with the aspect described above, but it can also be implemented in medical device in a healthcare environment independently of whether the aspect described above is also being used.

Briefly, in accordance with this aspect of the invention, a medical device 54 in the system 52 comprises a directional speaker or speaker array 56 that generates an audible alarm in a defined directional pattern (i.e. it does not emit the alarm sound uniformly around the medical device 54), and the directivity of the speaker or speaker array 56 is set so that the amount of sound energy being emitted towards a patient (and specifically the patient's head) on a bed associated with the medical device 54 is substantially less than the amount of sound energy being emitted into the rest of the room in which the patient is located (in other words the directional speaker 56 is configured to emit the alarm signal with spatial directivity such that the alarm signal is emitted substantially away from or not generally in the direction of the patient on the bed).

Furthermore, the medical device 54 is connected to a bed control unit 58 that is used to set and adjust the position and/or configuration of the patient bed, and the medical device 54 uses information from the bed control unit 58 relating to the current position or configuration of the patient bed (for example the height of the bed, whether the bed is configured so that the patient is sat up, etc.) or changes in the position or configuration of the patient bed to adjust or set the directivity of the speaker or speaker array 56 so that the alarm signal is emitted substantially away from the patient on the patient bed.

As noted above, the medical device 54 comprises a directional speaker or speaker array 56. As appreciated by those skilled in the art, emitting sound with directional characteristics can be realized very efficiently by speaker arrays, in which a number of identical or non-identical speakers are arranged next to each other.

The medical device 54 also comprises at least one sensor 60 for monitoring one or more physiological characteristics of a patient in the patient bed and/or for monitoring the operation of the medical device 54 (as appropriate depending on the purpose of the medical device). The medical device also comprises a processing unit 62 that is connected to the at least one sensor 60 and directional speaker or speaker array 56 and that controls the operation of the medical device 18. The directional speaker or speaker array 56 is used to generate an audible alarm signal in response to an alarm condition being detected by the sensor 60 and processing unit 62. A communication interface 64 is provided that is connected to the processing unit 62 and that enables communications between the medical device 18 and the bed control unit 58. The processing unit 62 is also configured to adjust or set the directivity of the directional speaker or speaker array 56.

In some embodiments, directivity adjustments can be realised by changing gain factors, frequency response and/or delays for signals sent from a control unit/amplifier to the driver of each of the speakers in the array 56. It will be appreciated that the beam pattern does not have to be uniform across an opening angle, but can also be split into two or more separate beams, with a minimum amount of energy being sent out between the beams. It will be appreciated by those skilled in the art that wave-field synthesis systems, di-poles and other driver combinations can be used as an alternative to multi-driver beamforming arrays.

As a further alternative, or in addition to the embodiments described above, the directional speaker or speaker array 56 may be configured so that the speaker or speaker array 56 can be physically moved (e.g. by a motor) in order to effect changes in the direction of the emitted sound.

The bed control unit 58 comprises a communication interface 66 that enables communication with the medical device 54, a processing unit 68 that is connected to the communications interface 66, one or more bed actuators 70 that are used to adjust the position or configuration of the patient bed in response to signals received from one or more bed adjustment controls 72 that can be operated by the patient or a healthcare staff member to adjust the position or configuration of the bed. In some embodiments, the controls 72 and bed actuators 70 can be used to adjust the height of the bed and/or adjust the patient between lying down and sitting up positions.

The processing unit 68 can determine the current position or configuration of the patient bed in response to feedback signals provided by the bed adjustment controls 72 or by the bed actuator(s) 70, and communicate this position or configuration to the medical device 54 through the communications interface 66. In alternative embodiments, a dedicated sensor can be provided on the bed that senses the position and/or configuration of the bed and that provides an appropriate signal to the processing unit 62 in the medical device 54. In other alternative embodiments, the patient could wear a sensor that detects the position and/or posture of the patient, or a camera can be provided in the patient room that observes the position and/or configuration of the bed.

In preferred embodiments, the directional speaker or speaker array 56 is configured so that it selectively radiates most of its sound energy in a horizontal plane, approximately at the height of the head of a person who is standing upright in the room, and can thus easily be recognized by staff members. At the same time (and in all embodiments of this aspect of the invention), the speaker or speaker array 56 is configured to radiate a highly reduced amount of acoustic energy in the direction of the head of the patient on the bed. This arrangement provides the advantage that the alarm can be heard by the relevant people in the patient room (i.e. the healthcare staff members), while minimising the amount of sound that is audible to the patient themselves.

Figure 5:
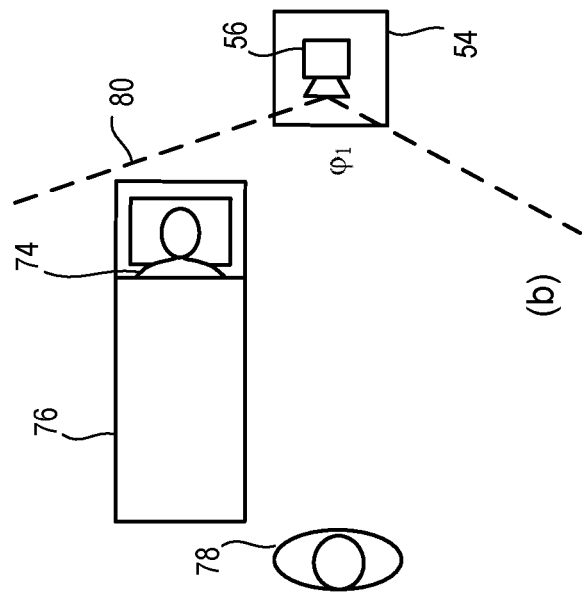
FIG. 5 is an illustration of the sound distribution pattern of the directional speaker when the patient bed is in a lowered position.
Figure 5:
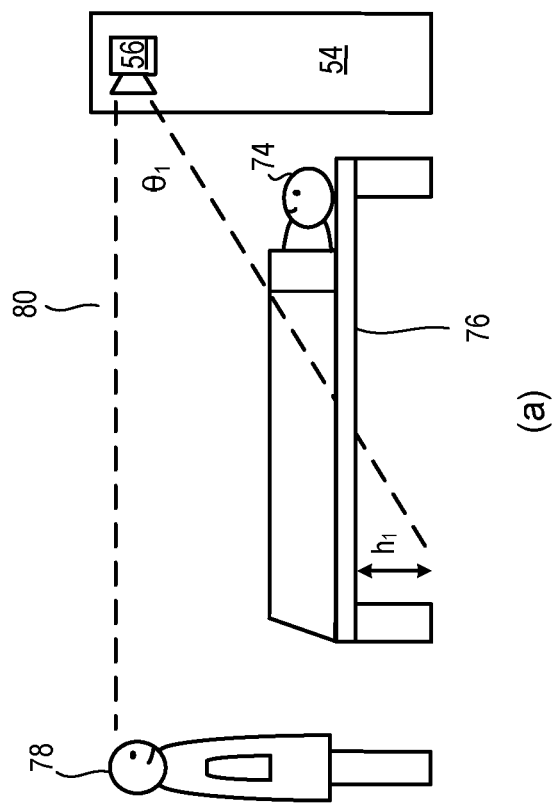

FIG. 5 is an illustration of a sound distribution pattern of the directional speaker when the patient bed is in a lowered position (with the height being denoted $h_1$) according to an embodiment. FIG. 5 shows both a side view of a patient 74 in a patient bed 76 (FIG. 5(*a*)) and a top view (FIG. 5(*b*)). The medical device 54 is positioned near to the patient bed 76 so that the patient 74 can be monitored and/or treated by the medical device 54 as required. A healthcare staff member 78 is also shown in the Figure.

Dashed lines 80 illustrate generally the directivity of the directional speaker or speaker array 56 in the medical device 54. It will be appreciated that the dashed lines show generally the direction in which the majority of the sound energy is radiated by the speaker or speaker array 56, with a relatively small amount of sound energy being radiated outside of these lines.

Figure 6:
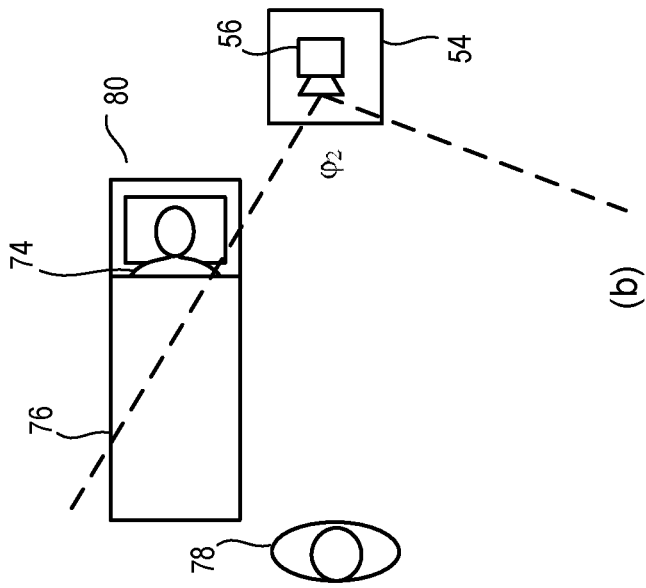
FIG. 6 is an illustration of the sound distribution pattern of the directional speaker when the patient bed is in a raised position.
Figure 6:
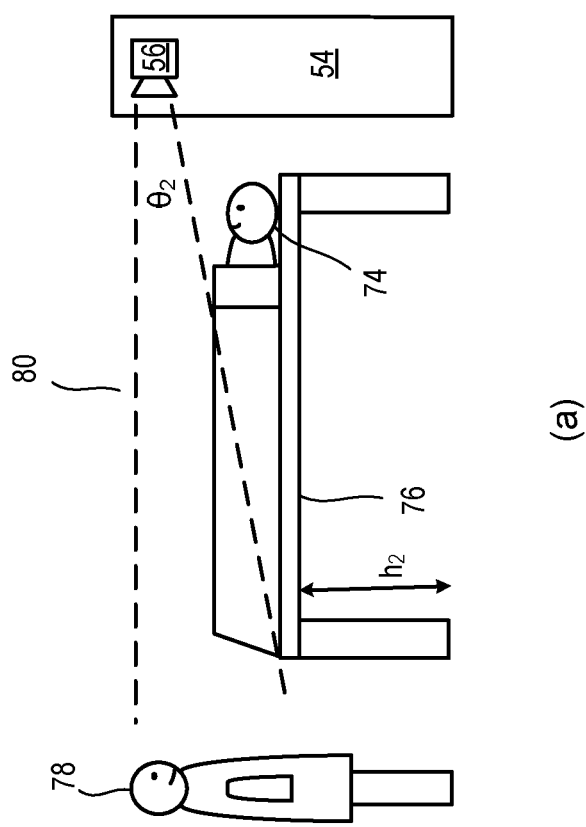

FIG. 6 is an illustration of an exemplary sound distribution pattern of the directional speaker when the patient bed is in a raised position (with the height being denoted $h_2$, with $h_2 > h_1$) according to an embodiment. As with FIG. 5, FIG. 6 shows both a side view of the patient 74 in the patient bed 76 (FIG. 6(*a*)) and a top view (FIG. 6(*b*)).

Thus, it can be seen from FIG. 5 that when the bed is in a lowered position the directivity of the directional speaker or speaker array 56 can be set so that it generally radiates in a horizontal plane above the height at which the head of the patient 74 is located and downwards to an angle $\theta_1$ from the horizontal. From the overhead view in FIG. 5(*b*), it can be seen that the azimuthal angle of the emitted sound is denoted $\phi_1$ and the sound radiates generally over the head of the patient. It can be seen from FIG. 6 that when the bed is in a raised position the directivity of the directional speaker or speaker array 56 is adjusted so that it continues to generally radiate in a horizontal plane, although the vertical extent of the emitted sound is reduced to avoid radiating the sound towards the patient's head (i.e. the angle of the sector over which the sound is emitted is denoted $\theta_2$, with $\theta_2 < \theta_1$) and the azimuthal angle (p of the emitted sound is also adjusted to an angle $\phi_2$ (where $\phi_2 < \phi_1$) to ensure that the majority of the sound energy of the alarm is not directed towards the head of the patient 74.

Figure 7:
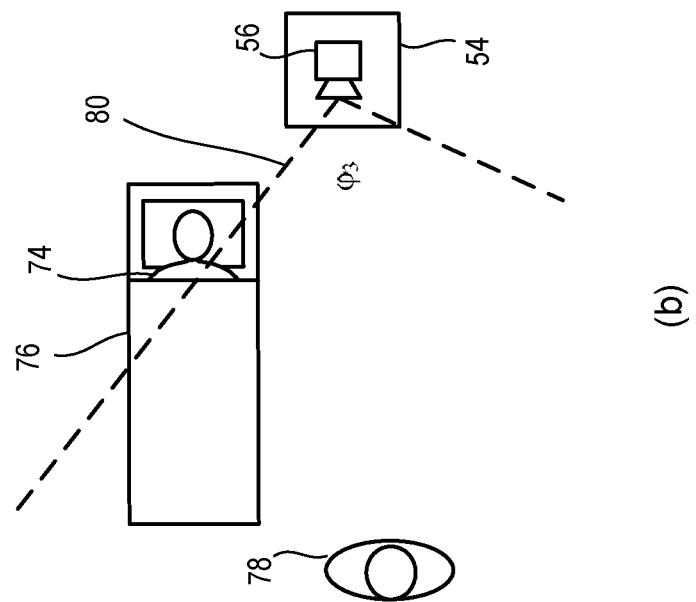
FIG. 7 is an illustration of the sound distribution pattern of the directional speaker when the patient bed is configured to allow the patient to sit upright.
Figure 7:
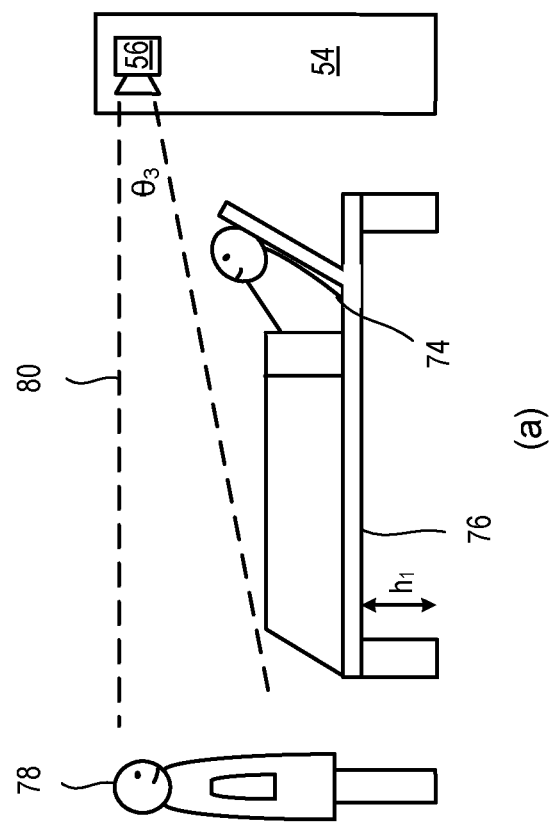

Likewise, a similar adjustment is made to the directivity of the directional speaker or speaker array 56 when the bed is adjusted so that the patient 74 is sat up, as shown in FIGS. 7(*a*) and (*b*). In FIG. 7(*a*), it can be seen that the sound is again being emitted generally in a sector defined by the horizontal plane and a radius angled downwards from the horizontal by an angle denoted $\theta_3$ (where $\theta_3 < \theta_1$) and again the azimuthal angle of the emitted sound is reduced compared to that shown in FIG. 5(*b*) (with the angle being denoted $\phi_3$ and $\phi_3 < \phi_1$).

Although FIGS. 6 and 7 show the adjustment of the directivity of the speaker or speaker array 56 in both the horizontal and vertical directions as the position of the bed 76 (and thus the position of the patient 74) changes, it will be appreciated that it may only be necessary to adjust the directivity of the speaker or speaker array 56 in one of the horizontal or vertical directions in order to ensure that the majority of the sound energy of the alarm is not directed towards the patient's head. It will also be appreciated that in some implementations the speaker or speaker array 56 may be configured such that it is only possible to adjust the directivity in one of the horizontal and vertical directions.

Figure 8:
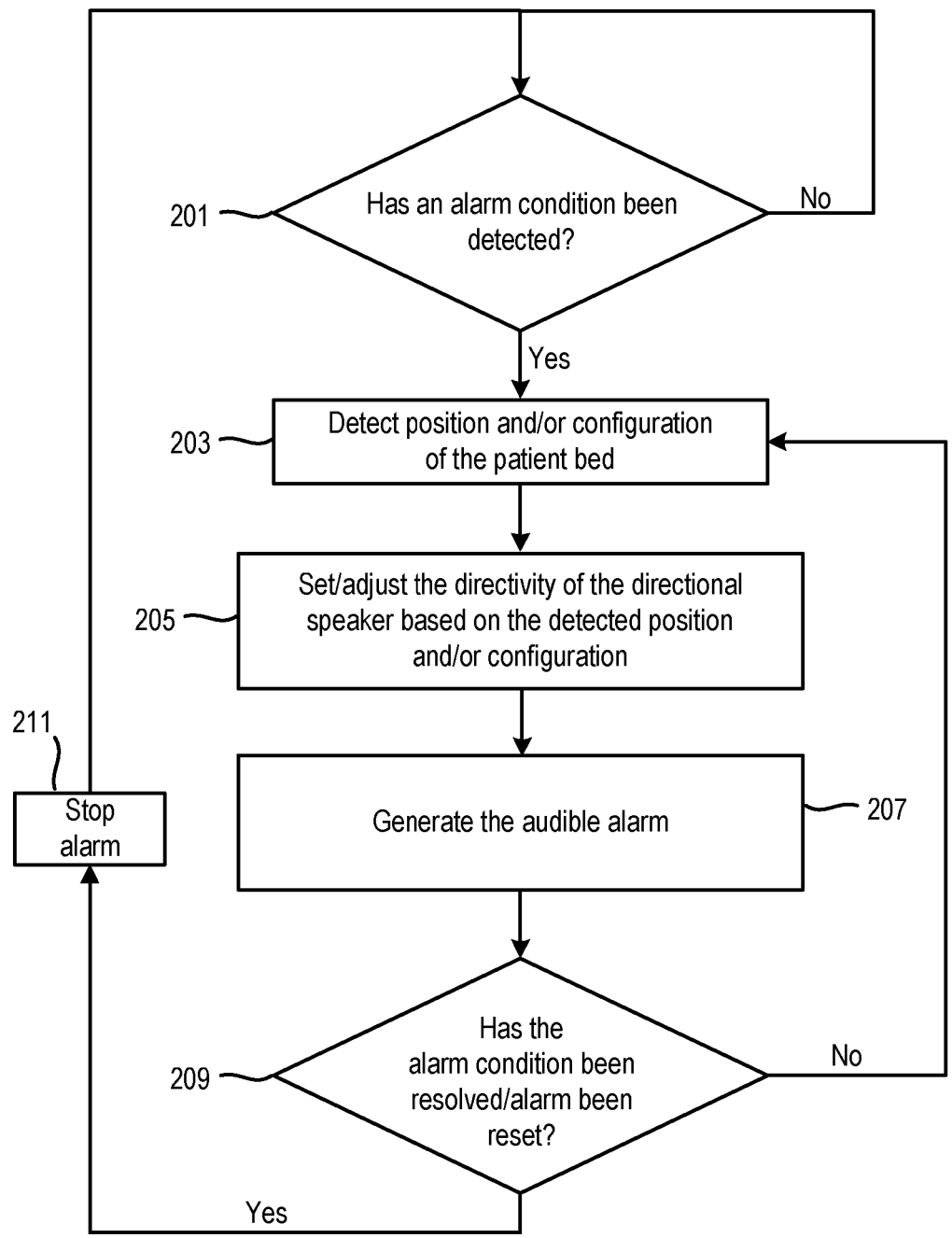
FIG. 8 is a flow chart illustrating a method of operating the system shown in FIG. 4.

FIG. 8 illustrates a method of operating the medical device 54 according to this aspect of the invention. In a first step, step 201, the processing unit 62 determines whether an alarm condition has been detected by the sensor 60 for the medical device 56. Step 201 repeats until an alarm condition exists.

If an alarm condition has been detected, the method moves to step 203 in which the processing unit 62 determines the position and/or configuration of the patient bed 76 (e.g. the height of the bed 76 and/or whether the bed 76 is configured to allow the patient 74 to sit up). Preferably the processing unit 62 determines the position and/or configuration of the bed 76 from signals received from the bed control unit 58.

Once the position and/or configuration of the bed 76 has been determined, the directivity required for the directional speaker or speaker array 56 is determined from this information so that sound emitted by the speaker or speaker array 56 is not generally emitted towards the head of the patient 74 (step 205). In some embodiments, the required directivity can be determined by looking up the appropriate settings for the directional speaker or speaker array 56 for the particular position and/or configuration of the patient bed 76 in a look-up table. Those skilled in the art will appreciate other ways in which the processing unit 62 can determine the required settings for the directional speaker or speaker array 56.

Once the directivity of the speaker or speaker array 56 has been set (or rather once the required settings for the speaker or speaker array 56 have been determined) in step 205, the processing unit 62 controls the speaker or speaker array 56 to generate the audible alarm with the required directivity (step 207).

While the alarm is being or continues to be generated by the speaker or speaker array 56, the processing unit 62 continues to monitor the position and/or configuration of the bed 76, and if it changes, the processing unit 62 can proceed to adjust the directivity of the speaker or speaker array 56 so that the disturbance to the patient 74 is minimised while allowing a healthcare staff member 78 in the room to be alerted (see the loop from step 209 back to step 203).

If the processing unit 62 determines that the alarm condition has been resolved or the alarm has been reset (step 209), for example through an action taken by a healthcare staff member 78, the processing unit 62 stops the generation of the audible alarm (step 211), and the method returns to step 201. Where this aspect of the invention is implemented alongside the first aspect of the invention described above, the action taken by the healthcare staff member 78 could include the staff member 78 entering the room or approaching the medical device 54 as detected by detection unit 20.

Therefore, this aspect of the invention provides a medical device (or a system comprising a medical device) and method for reducing the negative impact that alarm sounds have on patients while ensuring that healthcare staff are still adequately alerted.

In addition to the aspects of the invention described above, a further aspect of the invention is also provided. As with the aspects described above, it will be appreciated that this aspect of the invention can be implemented in a healthcare environment in conjunction with the aspects described above, but it can also be implemented in a healthcare environment independently of whether the aspects described above are also being used.

According to this aspect, healthcare staff members are provided with binaural sound-reproduction devices that can reproduce alarm sounds to the wearer in a way that provides the wearer with realistic spatial cues as the origin of the alarm condition. The reproduction device can comprise a wireless receiver for receiving the necessary alarm information from a central server or from individual alarming devices. The binaural device can be worn, for example, as a headset, and the device can detect or receive information about its relative location to the medical device with the alarm condition and the direction to the medical device/patient. When it is necessary to alert staff members to an alarm for a specific patient, the headsets can reproduce alarm sounds to (all or just selected) staff members in addition to or instead of generating sounds from the speaker built-in to the medical device. If the distance and the direction to the patient are known, the sound provided to the staff over the headset can contain realistic spatial cues enabled by binaural synthesis techniques. In some embodiments, the staff members wearing the binaural devices can perceive alarm sounds as coming from the patient bed, not from the headset itself, with the benefit that no alarm sounds are audible to patients. Clearly, the headsets should allow other sounds to be audible to the staff members, and one way to achieve this is to make the headsets capable of replicating all incoming sounds and reproducing them realistically to the ears of the wearer (for example in a similar way that hearing-aids work) or alternatively, the speakers of the headset can be located slightly away from wearer's ears.

The device according to this aspect can alternatively be a single (mono) speaker worn, for example, as a pendant by the staff members, which reproduces alarming sounds in which the volume level of the alarm sound is adjusted according to the relative distance to the patient (i.e. the device only provides a distance cue; no direction cues are provided).

Therefore, this aspect of the invention provides a wearable device (or a system comprising a wearable device) that allows the negative impact that alarm sounds have on patients to be reduced while ensuring that healthcare staff are still adequately alerted.

While the invention has been illustrated and described in detail in the drawings and foregoing description, such illustration and description are to be considered illustrative or exemplary and not restrictive; the invention is not limited to the disclosed embodiments.

Variations to the disclosed embodiments can be understood and effected by those skilled in the art in practicing the claimed invention, from a study of the drawings, the disclosure and the appended claims. In the claims, the word "comprising" does not exclude other elements or steps, and the indefinite article "a" or "an" does not exclude a plurality. A single processor or other unit may fulfil the functions of several items recited in the claims. The mere fact that certain measures are recited in mutually different dependent claims does not indicate that a combination of these measures cannot be used to advantage. A computer program may be stored/distributed on a suitable medium, such as an optical storage medium or a solid-state medium supplied together with or as part of other hardware, but may also be distributed in other forms, such as via the Internet or other wired or wireless telecommunication systems. Any reference signs in the claims should not be construed as limiting the scope.

The invention claimed is:

1. A system for use with a patient in a healthcare environment, the system comprising:
   a medical device configured to monitor or treat a patient, the medical device being for use in a room in which the patient is located and comprising an alarm unit configured to issue an audible alarm;
   a detection unit configured to detect whether at least one healthcare staff member is in the room in which the patient is located;
   a remote alarm unit configured to issue an alarm to alert the at least one healthcare staff member located outside the room in which the patient is located; and
   a control unit that is connected to the medical device, the detection unit and the remote alarm unit, the control unit being configured to:
   (i) control the alarm unit in the medical device to issue the audible alarm if (a) the medical device detects an alarm condition for the patient or the medical device and (b) the detection unit detects that the at least one healthcare staff member is in the room in which the patient is located; and
   (ii) control the remote alarm unit to issue the audible alarm to alert the at least one healthcare staff member located outside the room in which the patient is located in the event that (a) the medical device detects an alarm condition for the patient or the medical device and (b) the detection unit detects that no healthcare staff member is in the room in which the patient is located; and
   wherein the detection unit or a second detection unit is configured to detect a distance of the at least one healthcare staff member from the room in which the patient is located and the control unit is further configured to set the volume of the audible alarm issued by the remote alarm unit based on the distance of the at least one healthcare staff member from the room in which the patient is located.

2. A system as claimed in claim 1, wherein the control unit is further configured to prevent the alarm unit in the medical device from issuing the audible alarm in the event that the control unit controls the remote alarm unit to issue the alarm to alert the at least one healthcare staff member.

3. A system as claimed in claim 1, wherein the control unit is configured to control the alarm unit in the medical device to issue the audible alarm at a first volume level in the event that the medical device detects an alarm condition for the patient or the medical device and the detection unit detects that the at least one healthcare staff member is in the room in which the patient is located; and wherein the control unit is further configured to control the alarm unit in the medical device to issue the audible alarm at a second volume level in the event that the control unit controls the remote alarm unit to issue the alarm to alert the at least one healthcare staff member, wherein the second volume level is lower than the first volume level.

4. A system as claimed in claim 1, wherein the control unit is configured such that, if following the issue of an alarm by the remote alarm unit the detection unit detects that the at least one healthcare staff member is in or has entered the patient room, the control unit controls the remote alarm unit to cease the issue of the alarm and controls the alarm unit in the medical device to issue the audible alarm.

5. A system as claimed in claim 1, wherein the remote alarm unit comprises an alarm unit configured to issue the audible alarm and a visual indicator that is configured to be activated when the alarm unit in the remote alarm unit is controlled to issue the audible alarm.

6. A system as claimed in claim 5, wherein the control unit is configured to modulate the luminance of the visual indicator coherently with the volume of the audible alarm.

7. A system as claimed in claim 1, wherein the control unit is configured to reduce the volume of the audible alarm issued by the remote alarm unit as the distance of the at least one healthcare staff member from the room in which the patient is located decreases.

8. A system as claimed in claim 1, wherein the control unit is configured to increase the volume of the audible alarm issued by the remote alarm unit as the distance of the at least one healthcare staff member from the room in which the patient is located increases.

9. A system as claimed in claim 1, wherein the control unit is configured to set the volume of the audible alarm issued by the remote alarm unit to a first level when the at least one healthcare staff member is a first distance from the room in which the patient is located and a second level when the at least one healthcare staff member is a second distance from the room in which the patient is located, wherein the first level is greater than the second level and the first distance is greater than the second distance.

10. A method of operating a system for use with a patient in a healthcare environment, the method comprising:
    determining whether at least one healthcare staff member is in a room in which a medical device that is monitoring or treating the patient is located;
    detecting a distance of the at least one healthcare staff member from the room in which the patient is located; and
    in the event that an alarm condition for the patient or medical device is detected:
    (i) issuing an audible alarm from an alarm unit in the medical device if it is determined that the at least one healthcare staff member is in the room in which the patient is located; and
    (ii) issuing an audible alarm from a remote alarm unit to alert the at least one healthcare staff member located outside the room in which the patient is located if it is determined that no healthcare staff member is in the room in which the patient is located, and setting the volume of the audible alarm based on the distance of the at least one healthcare staff member from the room in which the patient is located.

11. A non-transitory computer-readable storage medium encoded with computer readable code embodied therein, the computer readable code being configured such that, on execution by one or more suitable computers or processing units, the one or more suitable computers or processing units are caused to execute the steps in the method of claim 10.

12. A medical device for use in monitoring or treating a patient in a patient bed, the position and/or configuration of the patient bed being adjustable to the needs of the patient, the medical device being for use in a room in which the patient bed is located, the medical device comprising:
    a sensor configured to monitor the patient and/or the operation of the medical device;
    a directional speaker configured to emit an alarm signal in the event that the sensor detects an alarm condition for the patient or the medical device, the directional speaker being configured to emit the alarm signal with spatial directivity such that the alarm signal is emitted substantially away from the patient on the patient bed;
    a control unit that is configured to determine the position and/or configuration of the patient bed or changes in the position and/or configuration of the patient bed and to adjust the spatial directivity of the directional speaker in response to the position and/or configuration of the patient bed or changes in the position and/or configuration of the patient bed so that the alarm signal is emitted substantially away from the patient on the patient bed.

13. A method of operating a medical device for use in monitoring or treating a patient in a patient bed, in which the position and/or configuration of the patient bed is adjustable to the needs of the patient, the medical device being for use in a room in which the patient bed is located, the medical device comprising a directional speaker configured to emit an alarm signal with spatial directivity; the method comprising:

determining the position and/or configuration of the patient bed or changes in the position and/or configuration of the patient bed; and in the event that an alarm condition for the patient or medical device is detected, adjusting or setting the spatial directivity of the directional speaker in response to the position and/or configuration of the patient bed or changes in the position and/or configuration of the patient bed so that the alarm signal is emitted substantially away from the patient on the patient bed.

\* \* \* \* \*